United States Patent
Cui et al.

(10) Patent No.: US 12,409,444 B2
(45) Date of Patent: Sep. 9, 2025

(54) METHOD FOR MAKING COPPER-CONTAINING CATALYSTS

(71) Applicant: JOHNSON MATTHEY PUBLIC LIMITED COMPANY, London (GB)

(72) Inventors: Youxin Cui, Billingham (GB); Monica Garcia, Billingham (GB); Pauline Elizabeth Glen, Billingham (GB); Norman Macleod, Billingham (GB); Michael Thomas Nicholson, Billingham (GB); Simone Roloff-Standring, Billingham (GB); Kaamila Un Din, Billingham (GB)

(73) Assignee: Johnson Matthey Public Limited Company, London (GB)

( * ) Notice: Subject to any disclaimer, the term of this patent is extended or adjusted under 35 U.S.C. 154(b) by 481 days.

(21) Appl. No.: 18/040,756

(22) PCT Filed: Sep. 6, 2021

(86) PCT No.: PCT/GB2021/052285
§ 371 (c)(1),
(2) Date: Feb. 6, 2023

(87) PCT Pub. No.: WO2022/069854
PCT Pub. Date: Apr. 7, 2022

(65) Prior Publication Data
US 2023/0278015 A1    Sep. 7, 2023

(30) Foreign Application Priority Data
Oct. 2, 2020  (GB) .................... 2015634

(51) Int. Cl.
| | |
|---|---|
| *B01J 23/80* | (2006.01) |
| *B01J 21/14* | (2006.01) |
| *B01J 37/03* | (2006.01) |
| *C01B 3/16* | (2006.01) |
| *C01B 3/32* | (2006.01) |
| *C07C 29/154* | (2006.01) |

(52) U.S. Cl.
CPC .............. *B01J 23/80* (2013.01); *B01J 21/14* (2013.01); *B01J 37/031* (2013.01); *C01B 3/16* (2013.01); *C01B 3/326* (2013.01); *C07C 29/154* (2013.01); *C01B 2203/0233* (2013.01); *C01B 2203/0238* (2013.01)

(58) Field of Classification Search
CPC ... B01J 21/08; B01J 21/12; B01J 21/14; B01J 23/06; B01J 23/72; B01J 23/80; B01J 37/03; B01J 37/031; B01J 37/035; C01B 3/16; C01B 3/326; C01B 2203/0233; C01B 2203/0238; C01B 2203/0405; C01B 2203/043; C01B 2203/1076; C01B 2203/1223; C07C 29/154; Y02P 20/141; Y02P 20/52

See application file for complete search history.

(56) References Cited

U.S. PATENT DOCUMENTS

| | | | |
|---|---|---|---|
| 6,048,820 A | 4/2000 | Takeuchi et al. | |
| 9,314,774 B2 | 4/2016 | Goto et al. | |
| 2011/0301022 A1* | 12/2011 | Murakami | ............... B01J 23/80 |
| | | | 502/343 |
| 2020/0197921 A1 | 6/2020 | Borchers et al. | |

FOREIGN PATENT DOCUMENTS

| | | |
|---|---|---|
| CN | 101306369 A | 11/2008 |
| CN | 101733109 A | 6/2010 |
| CN | 104379255 B | 5/2017 |
| CN | 107376922 A | 11/2017 |
| CN | 110612157 A | 12/2019 |
| EP | 0202824 A | 11/1986 |
| EP | 0742193 A1 | 11/1996 |
| EP | 2857095 A1 | 4/2015 |
| WO | 2008/047166 A2 | 4/2008 |
| WO | 2010/029325 A1 | 3/2010 |
| WO | 2017/072480 A1 | 5/2017 |
| WO | 2020/212681 A1 | 10/2020 |

* cited by examiner

*Primary Examiner* — Brian A Mccaig
(74) *Attorney, Agent, or Firm* — BakerHostetler

(57) ABSTRACT

A method for preparing a copper-containing catalyst is described comprising the steps of: (a) combining an acidic copper-containing solution with a first basic precipitant solution in a first precipitation step to form a first precipitate, (b) combining an acidic aluminium-containing solution, further comprising one or more metal compounds selected from copper compounds, zinc compounds and promoter compounds, with a second basic precipitant solution in a second precipitation step to form a second precipitate, (c) contacting the first and second precipitates together in a further mixing step to form a catalyst precursor, and (d) washing, drying and calcining the catalyst precursor to form the copper-containing catalyst, wherein a silica precursor is included in the first precipitation step, the second precipitation step or the precipitate mixing step, to provide a catalyst with a silica content, expressed as $SiO_2$, in the range of 0.1 to 5.0 wt %.

28 Claims, No Drawings

METHOD FOR MAKING COPPER-CONTAINING CATALYSTS

This invention relates to methods of manufacture of copper-containing catalysts, in particular copper-containing catalysts suitable for the water-gas shift reaction and methanol synthesis.

The copper-containing catalysts for such reactions are generally produced by forming into pellets small discrete particles of an intimate mixture of copper oxide and one or more oxidic materials, generally including zinc oxide, that are not substantially reduced under the conversion reaction process conditions. The intimate mixture is generally made by precipitation of copper compounds and compounds convertible to the other oxidic materials, and/or precipitation of the copper compounds in the presence of the other oxidic materials or compounds convertible thereto, followed by calcination to convert the precipitated copper compounds, and other components as necessary, to the oxides.

In some cases, the copper-containing catalyst has been modified with silica.

U.S. Pat. No. 6,048,820 discloses a silica-modified methanol synthesis catalyst produced using a single precipitation step employing aluminium nitrate. We have found that materials prepared using this method have relatively low activities.

EP0742193 discloses a process for manufacturing methanol in the presence of a catalyst obtainable by mixing, in a slurry state, (a) a beforehand prepared precipitation slurry of copper and zinc, with (b) an alumina precursor separately prepared from a water-soluble aluminium salt and a basic precipitant, to obtain a composition containing copper, zinc and aluminium, and washing, drying and then calcining the composition. Silica may be added to the composition.

CN101306369 discloses a catalyst preparation method comprising: (1), an acidic Al salt solution is precipitated by reaction with a solution of sodium carbonate which also contains sodium silicate; (2) Cu and Zn compounds are co-precipitated by reaction with an alkali metal carbonate; and (3) the two obtained co-precipitates are mixed, aged, then filtered, washed, dried and calcined. We have found catalysts prepared by this route using acidic aluminium solutions have relatively low initial activity and poor stability. This may be in part due to the high levels of retained alkali found in materials produced via this method.

We have found an alternative, simpler, preparation method that provides improved catalyst performance.

Accordingly the invention provides a method for preparing a copper-containing catalyst comprising the steps of: (a) combining an acidic copper-containing solution with a first basic precipitant solution in a first precipitation step to form a first precipitate, (b) combining an acidic aluminium-containing solution, further comprising one or more metal compounds selected from copper compounds, zinc compounds and promoter compounds, with a second basic precipitant solution in a second precipitation step to form a second precipitate, (c) contacting the first and second precipitates together in a further mixing step to form a catalyst precursor, and (d) washing, drying and calcining the catalyst precursor to form the copper-containing catalyst, wherein a silica precursor is included in the first precipitation step, the second precipitation step or the precipitate mixing step, to provide a catalyst with a silica content, expressed as $SiO_2$, in the range of 0.1 to 5.0 wt %.

The invention further includes a catalyst obtainable by the method and a process selected from methanol synthesis, methanol steam reforming and water-gas shift using the catalyst.

By precipitating the aluminium in the presence of one or more metal compounds selected from copper compounds, zinc compounds and promoter compounds, and by including a silica precursor, the present method provides catalysts having both high initial activity and excellent stability. The Applicants have found that the method produces a material which does not retain high levels of unwanted alkali, does not generate unwanted Dawsonite phases and generates a high surface area support phase and a small malachite crystallite size. Additionally, inclusion of the small amount of silicon produces catalysts having enhanced stability.

The method includes (a) combining an acidic copper-containing solution with a first basic precipitant solution in a first precipitation step to form a first precipitate. The solutions are both preferably aqueous. The acidic copper containing solution may be formed by dissolving copper or copper oxide in a suitable acid, such as nitric acid, or by dissolving one or more soluble copper compounds in water and adding acid if necessary. The one or more copper compounds may be selected from copper (II) nitrate, copper (II) acetate or other water-soluble copper compounds or salts. Copper (II) nitrate is preferred. The acidic copper-containing solution may usefully contain other components suitable for inclusion in copper catalysts. In particular the acidic copper-containing solution may contain one or more soluble zinc compounds. The one or more zinc compounds may be selected from zinc (II) nitrate, zinc (II) acetate or other water-soluble zinc compounds or salts. The acidic copper-containing solution may further comprise one or more promoter compounds selected from compounds of Mg, Co, Mn, V, Ti, Zr or rare earths. The promoters may stabilise the copper or enhance the properties of the support phase. Magnesium and zirconium compounds are preferred. Suitable magnesium and zirconium compound are magnesium nitrate and zirconyl nitrate. Suitable promoters for water-gas shift catalysts include potassium and/or caesium. An acid, preferably nitric acid, may be added to the acidic copper-containing solution if desired. Nitrates and nitric acid are preferred because they leave no catalyst poisons in the catalyst upon calcination. The first basic precipitant solution may comprise an alkali metal hydroxide or ammonium hydroxide, but this is less preferred and desirably the first basic precipitant solution preferably consists an alkali metal carbonate or bicarbonate, or mixtures thereof, so that copper hydroxycarbonate materials are precipitated. Sodium carbonate or potassium carbonate solutions are preferred. The first basic precipitant solution may further comprise one or more of the above promoter metals. The acidic copper-containing solution and first basic precipitant solutions may be added one to another in a first precipitation vessel but are preferably added simultaneously to the first precipitation vessel such that the pH in the first precipitation vessel is maintained between 6 and 9, preferably between 6 and 7. The precipitation step forms a precipitate, which is desirably mixed to form a slurry. If desired, the co-precipitate slurry may be aged to homogenise the precipitate and ripen crystalline materials. Ageing of the co-precipitate slurry may be carried out in a batch or semi-continuous procedure in a first ageing vessel whereby the aqueous slurry of the precipitated material is held in one or more stirred vessels for a period of time. Suspension of the co-precipitate in the liquid can be by mere stirring, the vigour of stirring depending on the tendency of the particles to settle and the viscosity. Alternatively, the co-precipitate slurry may be aged in a pulse-flow reactor as described in WO2008/047166, which is herein incorporated by reference. The precipitation and ageing may be performed at temperatures in the range of 10 to 80° C., but is preferably performed at elevated temperature, i.e. in the range 40 to 80° C., more preferably 50 to 80° C., especially 60 to 80° C., as this has been found to produce small crystallites that, after calcination, provide higher copper surface areas. The conditions can be chosen to produce crystalline compounds, for example of the Manasseite, Rosasite, Aurichalcite or Malachite type. The co-precipitation and ageing are preferably operated to produce malachite $[Cu_2(CO_3)(OH)_2]$, smithsonite $[ZnCO_3]$ and/or zincian malachite $[(Cu/Zn)_2(CO_3)(OH)_2]$ phases, which may be determined by XRD. However, in the present method, the first precipitate need not be aged.

The method further requires a step (b) combining an acidic aluminium-containing solution, further comprising one or more metal compounds selected from copper compounds, zinc compounds and promoter compounds, with a second basic precipitant solution in a second precipitation step to form a second precipitate. The acidic aluminium-containing solution may be formed by dissolving one or more aluminium compounds in water and adding acid if necessary. The one or more aluminium compounds may be selected from aluminium nitrate, aluminium acetate or other acidic water-soluble aluminium compounds or salts. Aluminium nitrate is preferred. In the present method, the acidic aluminium-containing solution contains one or more other components suitable for inclusion in copper catalysts. In particular, the acidic aluminium-containing solution contains one or more metal compounds selected from copper compounds, zinc compounds and promoter compounds. The one or more zinc compounds may be selected from zinc (II) nitrate, zinc (II) acetate or other water-soluble zinc compounds or salts. The one or more copper compounds may be selected from copper (II) nitrate, copper (II) acetate or other water-soluble copper compounds or salts. The one or more promoter compounds may be selected from compounds of Mg, Co, Mn, V, Ti, Zr or rare earths. Magnesium and zirconium compounds are preferred. Suitable magnesium and zirconium compound are magnesium nitrate and zirconyl nitrate. Suitable promoter compounds for water-gas shift catalysts include potassium nitrate and/or caesium nitrate. Whereas one or more copper compounds may be included in the second precipitation step it is preferred to include one or more zinc compounds and/or one or more promoter compounds, such as one or more magnesium compounds, in the acidic aluminium-containing solution. An acid, preferably nitric acid, may be added to the acidic aluminium-containing solution if desired.

In the second precipitation step (b), one or more metal compounds selected from copper compounds, zinc compounds and promoter compounds are co-precipitated with the aluminium. Where copper is included, the amount of copper included in the second precipitation may be in the range 0.5 to 20 wt % of the total copper in the catalyst, preferably 0.5 to 10 wt % of the total copper in the catalyst. Where zinc is included, the amount of zinc included in the second precipitation may be in the range 0.5 to 50 wt % of the total zinc in the catalyst, preferably 0.5 to 40 wt % of the total zinc in the catalyst, more preferably 0.5 to 30 wt % of the total zinc in the catalyst. Where promoters, such as magnesium or zirconium are included, the amount of promoter metal in the second precipitation may be in the range 0.5 to 100 wt % of the total promoter metal added. Precipitation of the aluminium compounds using carbonate precipitants in the absence of copper, zinc or promoter metals can form Dawsonite-type phases, which can be detrimental to the initial activity and long-term stability of the catalyst.

The second basic precipitant solution used in the second precipitation step may comprise alkali metal hydroxide, or an alkali metal carbonate, bicarbonate or mixtures thereof. Preferably the second basic precipitant solution consists of an alkali metal hydroxide. The alkali metal hydroxide may be sodium or potassium hydroxide or mixtures thereof.

Preferably the second precipitation step consists of combining an aqueous acidic aluminium-containing solution, such as aluminium nitrate solution, containing one or more zinc compounds, such as zinc nitrate, and/or promoter compounds, such as magnesium nitrate and/or zirconyl nitrate, with an aqueous second basic precipitant solution, especially a sodium or potassium hydroxide solution. The acidic aluminium-containing solution and second basic precipitant solution may be added one to another in a second precipitation vessel but are preferably added simultaneously to a second precipitation vessel such that the pH in the second precipitation vessel is maintained between 5 and 9, preferably between 6 and 8. The second precipitation step is preferably mixed or agitated thereby forming a slurry of the precipitate. Optional ageing of the precipitate slurry may be carried out using the methods described for the first precipitate. Ageing of the second precipitate is preferred. The precipitation and ageing may be performed at temperatures in the range of 10 to 80° C. but is preferably performed in the range 20 to 70° C. This has been found to produce suitable aluminium-containing support phases with high surface areas.

It will be understood that step (a) and step (b) above may be performed in any order, i.e. step (a) may be performed before or after step (b), or step (a) and step (b) may be performed simultaneously. The steps conveniently may be performed in separate precipitation vessels.

The method further requires a step (c) of contacting the first and second precipitates together in a mixing step to form a catalyst precursor. This step may be performed by recovering the precipitates from the first and second precipitation steps, for example by filtration or centrifuge, and then combining the recovered precipitates in a slurry of water or other suitable solvent. It is more convenient, however, to combine the slurries of the first and second precipitates together in a mixing vessel. It is preferred that neither of the precipitates is separated and washed prior to the combining step (c).

The first precipitate may be added to the second precipitate or vice versa, or the two slurries may be combined simultaneously at a controlled rate. Either precipitate may be subjected to an ageing step prior to mixing with the other precipitate or may be added without previously being aged. Preferably, the second precipitate is aged prior to mixing with an unaged first precipitate, after which the mixed precipitate slurry is subjected in step (c) to a final ageing step. This optional final ageing step may be carried out using the methods described above for the first precipitate. Admixture of the precipitate slurries may be performed with stirring or agitation and the resulting mixture held at elevated temperature in the contacting vessel to allow the mixing between the precipitates to occur.

In some embodiments, step (c) may be performed at the same time as step (a) or step (b), i.e. the solutions from step (a) may be added to the precipitate of step (b) or the solutions of step (b) may be added to the precipitate of step (a). In one arrangement, the first precipitation step (a) and the precipitation contacting step (c) occur simultaneously in the same vessel.

The resulting mixture may be allowed to mix for a period of 0.1 to 24 hours, at temperatures in the range 40 to 80° C., more preferably 50 to 80° C., especially 60 to 80° C. After the mixing and ageing process has taken place, the resulting catalyst precursor may conveniently be recovered by filtration, decanting or centrifuging.

In the present method, a silica precursor is included in the first precipitation step (a), the second precipitation step (b) and/or the contacting step (c), to provide a catalyst with a with a silica content, expressed as $SiO_2$, of 0.1 to 5.0 wt %. We have found that lower levels of silica are surprisingly superior in terms of stability. Hence in preferred embodiments the silica content of the calcined catalyst, expressed as $SiO_2$, is in the range 0.1 to 3% by weight, 0.1 to 2% by weight and especially 0.2 to 1.0% by weight.

The silica precursor may suitably be a colloidal silica or silica sol and/or a water-soluble silicon compound, such as an alkali metal silicate, e.g. potassium silicate. Organo-silicates, including alkyl-silicates such as tetramethyl-orthosilicate and tetraethyl-orthosilicate may also be used. The silica stabilises the copper during use and thereby improves the long-term activity of the catalyst compared to catalysts without silica.

If an acidic silica sol is used, it may be added in the first precipitation step to the acidic copper-containing solution and/or added to the first precipitation vessel and/or the first ageing vessel, if present. Similarly, a silica sol may be added in the second precipitation step to the acidic aluminium-containing solution and/or added to the second precipitation vessel and/or the second ageing vessel, if present. A silica sol may also be added to the mixture of precipitates in the contacting step (c). Particularly suitable silica sols comprise aqueous dispersions of colloidally dispersed silica having a particle size in the range of 10-20 nm. The pH of the dispersion may be <7, preferably in the range 2 to 4. The silica concentration in the sol may be 100-400 g/litre. Such sols are available commercially as, for example, Nissan Chemicals Snowtex-O and Grace Ludox HSA.

If a water-soluble silicate, such as an alkali metal silicate, or a basic silica sol is used, it may be added in the first precipitation step to the alkali metal carbonate solution and/or to the first precipitation vessel and/or the first ageing vessel, if present. Similarly, an alkali metal silicate or basic silica sol may be added in the second precipitation step to the basic precipitant solution and/or to the second precipitation vessel and/or the second ageing vessel, if present. An alkali metal silicate or basic silica sol may also be added to the mixture of precipitates in the contacting step (c). Suitable alkali metal silicates are sodium silicates and potassium silicates. Such alkali silicates are commercially available, for example, as PQ Corporation Kasil 1, PQ Corporation Kasolv 16 or Zaclon LLC Zacsil 18. The amount of silicon, expressed as $SiO_2$, in the alkali metal silicate solution may be in the range 5-40% wt % preferably 15-30 wt %. Where an alkali metal silicate is used, the alkali metal in the alkali metal silicate may match the alkali metal in the basic precipitant solution or alkali metal aluminate.

If an organo-silicate, such as an alkyl-silicate of formula $Si(OR)_4$ where R=C1-C4 alkyl, is used, because it will hydrolyse when contacted with water, it is preferably added to the first and/or second precipitation vessels, the first and/or second ageing vessels, or to the mixed precipitates in the contacting step (c).

In step (d), the recovered catalyst precursor is washed to remove residual soluble salts that might act as poisons or contaminants during use of the catalysts. Washing of the catalyst precursor may be performed using conventional equipment such as plate-and-frame filter presses, centrifuges or other suitable washing equipment, for example by re-slurrying the catalyst precursor one or more times in salt-free water, or by dynamic cross-flow filtration using an Artisan thickener or Shriver thickener before recovery. For methanol synthesis catalysts, the alkali metal content of the dried catalyst precursor should desirably be reduced to below 0.2% wt, preferably below 0.1% wt, calculated as the respective alkali metal oxide on the dried material on a loss-free basis.

The method further requires steps of drying and calcining the catalyst precursor to form the copper-containing catalyst. The drying may comprise heating the damp mixture in discrete stages or continuously over an extended period until the maximum temperature is reached.

The drying step may be performed at temperatures in the range of 90 to 150° C., preferably 90 to 130° C. under air or an inert gas using conventional drying equipment such as in an oven, rotary drier, spray drier or similar equipment.

The dried composition is typically in the form of a powder. The average particle size (as determined by sieve fractions, i.e. the weight-average particle size) may be in the range of 10-1000 m or 10-300 m (microns). The dried composition may comprise one or more hydroxycarbonates of copper and zinc, as well as alumina and silica or their compounds.

The dried composition is calcined and desirably shaped to form the catalyst. The dried composition may be calcined, i.e. heated, to convert the copper and any zinc compounds, and any promoter compounds, to their respective oxides prior to shaping or, less preferably, the dried composition may be formed into shaped units before calcination. This latter method is less preferred because the calcination of shaped units generally reduces their strength and makes it more difficult to control pellet density. The calcination may be performed at temperatures in the range of 250 to 500° C. preferably 280 to 450° C., more preferably 280 to 350° C. Lower temperatures provide lower pellet stabilities, whereas higher temperatures significantly reduce the initial activity created by the high copper dispersion. Calcination may be performed under air or an inert gas such as nitrogen, but air or another oxygen-containing gas is preferred. The calcined product is typically in the form of a powder.

The catalyst is preferably pelleted. The dried or calcined powder may therefore be subjected to pelleting, optionally after pre-compacting the powder, which can improve the pelleting process. The pellet may suitably be a cylindrical pellet. Cylindrical pellets for carbon oxide conversion processes suitably have a diameter in the range of 2.5 to 10 mm, preferably 3-10 mm and an aspect ratio (i.e. length/diameter) in the range of 0.5 to 2.0. Alternatively, the shaped unit may be in the form of rings. In one embodiment, the shaped unit is in the form of a cylinder having two or more, preferably 3 to 7 grooves running along its length. Suitable domed cylindrical shapes having one or more flutes are described in our WO2010/029325 and WO2017/072480, herein incorporated by reference.

Pellets, particularly cylindrical pellets with flat or domed ends as described above, are desirably made with pellet densities in the range of 1.8 to 2.5 g/cm$^3$, preferably 1.9 to 2.4 g/cm$^3$. The pellet density may readily be determined by calculating the volume from the pellet dimensions and measuring its weight. As the density is increased, the interstitial volume in the shaped units is reduced, which in turn reduces the permeability of reacting gases. Therefore, for densities >2.4 g/cm$^3$ the reactivity of the catalyst may be less than optimal, despite the high volumetric copper content. For densities <1.8 g/cm$^3$ the crush strengths may be insufficient for long-term use in modern carbon-oxide conversion processes.

The relative amounts of copper-containing solution, zinc-containing solution, aluminium-containing solution, promoter solution and silica precursor may be adjusted to produce compositions suitable for use as catalysts. The copper oxide content of the calcined catalyst (expressed as CuO) may be in the range of 30 to 70% by weight. Within this range a copper oxide content in the range of 50 to 70% by weight, preferably 60 to 70% by weight, is of general application for methanol synthesis, whereas for the water-gas shift reaction, the copper oxide content may be lower, particularly in the range of 30 to 60% by weight. Suitably, the copper (II) oxide content of the calcined catalyst is in the range 50 to 68% by weight. As stated above, zinc is preferably included in the first precipitation step. The weight ratio of Cu:Zn (expressed as CuO:ZnO) in the calcined catalyst may be 1:1 or higher but is preferably in the range of 2:1 to 3.5:1, especially 2.5:1 to 2.75:1 for methanol synthesis catalysts and in the range of 1.4:1 to 2.0:1 for water-gas shift catalysts. In the methanol synthesis catalysts, the catalyst preferably contains 15 to 50% by weight, preferably 20-35% by weight zinc oxide.

The calcined catalyst contains alumina, which may be present in an amount in the range of 5 to 40% by weight preferably 6 to 20% by weight, expressed as $Al_2O_3$. The alumina may be present as a boehmite AlOOH, and/or as a transition alumina, such as gamma alumina, and/or as a metal aluminate, such as zinc aluminate.

The calcined catalyst contains silica and may have a Si:Al atomic ratio in the range of 0.004 to 0.2:1. The amount of silica in the catalyst appears to be optimal when the Si:Al atomic ratio is in the range of 0.03 to 0.09:1. The amount of silica in the catalyst is therefore relatively low, and may be present in the calcined catalyst in an amount in the range of 0.1 to 5.0% by weight, preferably 0.1 to 2.0% by weight, more preferably 0.2 to 1.0% by weight. Higher amounts of silica reduce the activity of the catalyst and may generate acidic sites that reduce selectivity in methanol production.

If a promoter is included in the first and/or second precipitation steps, the calcined catalyst may contain promoter oxide, e.g. magnesium oxide and/or zirconium oxide, in an amount in the range of 0.5 to 5% by weight.

Preferred methanol synthesis catalysts consist essentially of oxides of copper, zinc, aluminium, magnesium and silicon.

The dried catalyst made by the method may have a malachite, e.g. zincian malachite, crystal size of less than 10 nm, preferably less than 9 nm, more preferably less than 8 nm. The crystal size may be greater than 3 nm. The malachite crystal size may be determined using X-ray Diffraction (XRD).

The calcined catalyst made by the method may have a copper surface area ≥40 m$^2$/g catalyst, preferably ≥50 m$^2$/g catalyst, more preferably ≥55 m$^2$/g catalyst. Copper surface areas up to about 60 or 65 m$^2$/g catalyst may be achieved. These surface areas are suitably determined on a sample of crushed catalyst pellets. The copper surface area may be readily established by reactive frontal chromatography, for example as described in EP-A-0202824.

The BET surface area of the shaped catalyst, as determined by nitrogen physisorption (according to ASTM Method D 3663-03), may be ≥75 m$^2$/g, preferably ≥100 m$^2$/g, more preferably ≥115 m$^2$/g. BET surface areas up to about 130 m$^2$/g may be achieved. The BET surface areas are suitably determined on a sample of crushed catalyst pellets.

In the catalyst, the zinc oxide, alumina, silica, and promoter oxides if present, are not substantially reduced to metal under the carbon oxide conversion process conditions and are generally present as the oxides in the catalyst. In contrast, the copper oxide is more readily reduced to the active elemental form. The copper may be reduced either ex-situ or in-situ to form catalytically active copper metal crystallites before use.

The catalysts prepared by the method may be used in any carbon oxides conversion process, comprising reacting a carbon oxide containing process gas containing at least one of carbon monoxide and carbon dioxide and additionally containing hydrogen and/or steam, in the presence of the catalyst. The term "carbon oxides" herein includes at least one of carbon monoxide and carbon dioxide. The catalysts are of particular utility in methanol synthesis, methanol steam reforming and in the water-gas shift reaction.

The catalyst may be pre-activated in-situ by exposing it to a reducing gas stream, preferably comprising hydrogen, to convert the copper oxide into elemental copper. Thus, the method may further comprise the steps of (i) activating the catalyst by contacting it with a reducing gas stream and (ii) reacting a carbon oxide containing process gas containing at least one of carbon monoxide and carbon dioxide and additionally containing hydrogen and/or steam, in the presence of a catalyst to form a product stream. Activation may be performed using a hydrogen containing gas, including synthesis gas comprising hydrogen and carbon oxides, at temperatures above 80° C. and at pressures in the range of 1-50 bar g. The maximum reduction temperature is desirably 150 to 300° C.

The invention includes processes using the catalyst, in particular:

A. Methanol synthesis in which a gas mixture containing one or both carbon oxides (i.e. carbon monoxide and/or carbon dioxide) and hydrogen is passed over the catalyst at a temperature in the range of 200-320° C., a pressure in the range of 20-250, especially 30-120, bar abs and a space velocity in the range of 500-20000 h$^{-1}$. The process can be on a once-through, or a recycle, basis and can involve cooling by indirect heat exchange surfaces in contact with the reacting gas, or by subdividing the catalyst bed and cooling the gas between the beds by injection of cooler gas or by indirect heat exchange. For this process, the catalyst preferably contains copper, zinc oxide and optionally magnesia, with alumina and silica. The catalysts may be used in methanol synthesis processes in which natural gas is steam reformed or autothermally reformed with oxygen to produce a synthesis gas containing carbon monoxide, carbon dioxide and hydrogen, or in processes where the synthesis gas is richer in carbon monoxide and is derived by the gasification of coal or biomass. The catalyst may be of particular use in methanol synthesis processes where a synthesis gas is formed essentially from hydrogen and carbon dioxide, especially where the hydrogen and/or carbon dioxide are recovered only from renewable sources, such as from the electrolysis of water for hydrogen and $CO_2$-recovery from waste gases, such as combustion gas or landfill gas.

B. Modified methanol synthesis in which the catalyst contains also free alumina of surface area 50-300 m$^2$ g$^{-1}$, or another acidic catalyst, so that the synthesis product is relatively rich in dimethyl ether. Temperatures, pressures and space velocities are similar to those for methanol synthesis but the synthesis gas may contain hydrogen and carbon monoxide in a molar ratio of less than 2.

C. Low temperature shift reaction in which a gas containing carbon monoxide (preferably under 4% v/v on a dry basis) and steam (steam to total dry gas molar ratio typically in range of 0.3 to 1.5) is passed over the catalyst in an adiabatic fixed bed at an outlet temperature in the range of 200 to 300° C. at a pressure in the range of 15-50 bar abs. Usually the inlet gas is the product of "high temperature shift" in which the carbon monoxide content has been decreased by reaction over a high temperature shift catalyst, such as an iron or zinc aluminate catalyst, at an outlet temperature in the range of 400 to 500° C., followed by cooling by indirect heat exchange. The outlet carbon monoxide content from the low temperature shift step is typically in the range of 0.1 to 1.0%, especially under 0.5% v/v on a dry basis.

D. Medium temperature shift in which the gas containing carbon monoxide and steam is fed at a pressure in the range of 15-50 bar abs to the catalyst at an inlet temperature typically in the range of 200 to 240° C. although the inlet temperature may be as high as 280° C., and the outlet temperature is typically up to 300° C. but may be as high as 360° C. These conditions are more severe than in B, such that the new catalyst is expected to be especially advantageous.

E. Low-medium temperature shift with heat exchange (also termed isothermal shift), in which the reaction in the catalyst bed occurs in contact with heat exchange surfaces. The coolant conveniently is water under such a pressure such that partial, or complete, boiling takes place. A suitable pressure is 15 to 50 bar abs and the resulting steam can be used, for example, to drive a turbine or to provide process steam for shift, or for an upstream stage in which the shift feed gas is generated. The water can be in tubes surrounded by catalyst or vice versa.

F. Methanol reforming in which a gaseous methanol stream is combined with steam and/or carbon dioxide and subjected to reaction, typically at temperatures in the range of 250 to 360° C. and at pressures typically in the range of 10 to 30 bar abs, over the catalyst to generate a gas mixture containing hydrogen and carbon oxides. The hydrogen may be recovered from the gas mixture using conventional separation methods such as pressure-swing adsorption or hydrogen-permeable membranes.

The invention is now further described by reference to the following Examples.

In the Examples, unless otherwise stated, first precipitates were prepared at a 2-6 litre scale by simultaneous addition of an aqueous mixed metal nitrate solution and an aqueous alkali metal carbonate solution to a stirred precipitation vessel held at 65 to 70° C. The first precipitates were unaged. Second precipitates were prepared at a 0.5-4 litre scale by simultaneous addition of an aqueous mixed metal nitrate solution and an aqueous alkali metal hydroxide or carbonate solution to a stirred precipitation vessel held at 65 to 70° C. Ageing of the slurries of the second precipitates was performed in a separate stirred vessel for up to 2 hours, again at 65 to 70° C. The first and second slurries were combined and mixed in a 3-8 litre vessel for up to 2 hours. The silica precursor was added by various means at different points in the preparation process. The mixed precipitate slurries were filtered and washed with demineralised water. Drying and calcination of the washed precipitate was, unless otherwise stated, carried out at 110° C. and 300° C. respectively. The resulting powders were compacted into a shaped unit, which was subsequently crushed into grit particles suitable for testing. The silica sol used throughout was Snowtex-O (Nissan Chemicals). Potassium silicate used was Kasil 1 (PQ Corporation). Sodium silicate used was sodium metasilicate nonahydrate (Sigma Aldrich). Unless otherwise stated, in all cases the weight percentages of the metal oxides in the catalyst are determined on a loss-free basis. A particularly suitable method for determining the metal oxide content on a loss-free basis is to heat the catalyst to 900° C. for 2 hours in air to remove volatiles before measuring the metal oxide contents. The heat-treated catalyst may be stored under anhydrous conditions. The metal oxide content of the catalysts may be determined using any suitable elemental analysis technique, such as X-ray fluorescence spectroscopy (XRF) using known techniques. Copper surface areas were determined using reverse frontal chromatography as follows: catalyst pellets were crushed and sieved to a particle size of 0.6 to 1.00 mm. About 2.0 g of the crushed material was weighed into a stainless steel tube and heated to 68° C. and purged with helium for 2 minutes. Then, the catalyst was reduced by heating it in a flow of 5% vol H2 in helium, at 4° C./min up to 230° C. and holding at this temperature for 30 minutes until fully reduced. The reduced catalyst was cooled to 68° C. under helium. The reduced catalyst then had a 2.5% vol $N_2O$ in helium gas mixture passed over the catalyst. The evolved gases were passed through a gas chromatograph and the $N_2$ evolution was measured. The discharged catalyst was weighed and from this, the copper surface area per gram of discharged catalyst was calculated.

BET surface areas were determined on the crushed pellet grit, after drying, by nitrogen physisorption using a Micromeritics 2420 ASAP physisorption analyser in accordance with ASTM Method D 3663-03; Standard Test for Surface Area. Nitrogen was used as the adsorbate and the measurements carried out at liquid nitrogen temperature (77K). The cross-sectional area of a nitrogen molecule was taken as 16.2 Å$^2$. Samples were outgassed prior to analysis by purging with dry nitrogen gas for a minimum of 1 hour at an optimal temperature. Five relative pressure/volume data pairs were obtained over the relative pressure region of 0.05 to 0.20 P/Po inclusive. The equilibration time for each point was 10 seconds.

Malachite crystal sizes of dried intermediates were determined from powder XRD patterns. These were collected on a Bruker D8 diffractometer equipped with a Göbel mirror, Lynxeye detector and a copper x-ray tube. Phase identification was completed using the Bruker EVA v5.1.0.5 software. Crystallite size values were estimated using Bruker Topas v6. In the Rietveld method the usual parameters (sample displacement, scale factors, background coefficients, unit cell parameters and peak shape) were refined. Atomic positions were fixed and not refined. Reported crystallite size values were obtained from an integral breadth based LVol calculation using Lorentzian and Gaussian type component convolutions.

EXAMPLE 1

An oxidic catalyst with the molar ratio Cu:Zn:Al:Si of 4.6:1.7:1.0:0.04 and a copper oxide content of 65.7 wt. % was prepared. In a first precipitation step, a mixed metal solution comprising nitrates of copper and zinc was co-precipitated with a sodium carbonate solution at a pH of 6.4-6.7 and a temperature of 65° C. to form a first precipitate slurry. In a second precipitation step, a mixed metal solution comprising nitrates of aluminium and zinc, which contained a silica sol, was precipitated with a sodium hydroxide solution at a pH of 7.0-7.2 and a temperature of 75° C. to form a second precipitate slurry, and the second precipitate slurry subsequently aged at 65° C. for up to 2 hours. The second precipitate slurry was added to the first precipitate slurry, and the mixture was aged at 70° C. with stirring for up to 1.3 hours. The resulting catalyst precursor slurry was dewatered, washed with demineralised water, then dried and calcined in air at 300° C. for 6 hours. The first precipitate contained 84 wt % of the total zinc in the calcined catalyst. The second precipitate contained 16 wt % of the total zinc in the calcined catalyst.

EXAMPLE 2

An oxidic catalyst with the molar ratio Cu:Zn:Al:Si of 4.5:1.7:1.0:0.03 and a copper oxide content of 65.3 wt. % was prepared. In a first precipitation step, a mixed metal solution comprising nitrates of copper and zinc was co-precipitated with a potassium carbonate solution at a pH of 6.4-6.7 and a temperature of 65° C. to form a first precipitate slurry. In a second precipitation step, a mixed metal solution comprising nitrates of aluminium and zinc, which contained a silica sol, was precipitated with a potassium hydroxide solution at a pH of 7.0-7.2 and a temperature of 75° C. to form a second precipitate slurry, and the second precipitate slurry aged at 65° C. for up to 2 hours. The remaining mixing, drying and calcining steps were carried out according to the method of Example 1. The first precipitate contained 84 wt % of the total zinc in the calcined catalyst. The second precipitate contained 16 wt % of the total zinc in the calcined catalyst.

EXAMPLE 3

An oxidic catalyst with the molar ratio Cu:Zn:Al:Si of 4.6:1.7:1.0:0.07 and a copper oxide content of 65.3 wt. % was prepared. In a first precipitation step, a mixed metal solution comprising nitrates of copper and zinc was co-precipitated with a potassium carbonate solution at a pH of 6.4-6.7 and a temperature of 65° C. to form a first precipitate slurry. In a second precipitation step, a mixed metal solution comprising nitrates of aluminium and zinc, which contained a silica sol, was precipitated with a potassium hydroxide solution at a pH of 7.0-7.2 and a temperature of 75° C. to form a second precipitate slurry, and the second precipitate slurry aged at 65° C. for up to 2 hours. The remaining mixing, drying and calcining steps were carried out according to the method of Example 1. The first precipitate contained 84 wt % of the total zinc in the calcined catalyst. The second precipitate contained 16 wt % of the total zinc in the calcined catalyst.

EXAMPLE 4

An oxidic catalyst with the molar ratio Cu:Zn:Al:Si of 4.3:1.6:1.0:0.03 and a copper oxide content of 65.1 wt. % was prepared. In a first precipitation step, a mixed metal solution comprising nitrates of copper and zinc was co-precipitated with a potassium carbonate solution at a pH of 6.4-6.7 and a temperature of 65° C. to form a first precipitate slurry. In a second precipitation step, a mixed metal solution comprising nitrates of aluminium and zinc was precipitated with a potassium hydroxide solution containing potassium silicate at a pH of 7.0-7.2 and a temperature of 75° C. to form a second precipitate slurry, and the second precipitate slurry aged at 65° C. for up to 2 hours. The remaining mixing, drying and calcining steps were carried out according to the method of Example 1. The first precipitate contained 84 wt % of the total zinc in the calcined catalyst. The second precipitate contained 16 wt % of the total zinc in the calcined catalyst.

EXAMPLE 5

An oxidic catalyst with the molar ratio Cu:Zn:Al:Mg:Si of 4.4:1.6:1.0:0.1:0.03 and a copper oxide content of 64.8 wt. % was prepared. In a first precipitation step, a mixed metal solution comprising nitrates of copper, zinc and magnesium was co-precipitated with a potassium carbonate solution containing potassium silicate at a pH of 6.4-6.7 and a temperature of 65° C. to form a first precipitate slurry. In a second precipitation step, a mixed metal solution comprising nitrates of aluminium and zinc was precipitated with a potassium hydroxide solution at a pH of 7.0-7.2 and a temperature of 75° C. to form a second precipitate slurry, and the second precipitate slurry aged at 65° C. for up to 2 hours. The remaining mixing, drying and calcining steps were carried out according to the method of Example 1. The first precipitate contained 84 wt % of the total zinc in the calcined catalyst. The second precipitate contained 16 wt % of the total zinc in the calcined catalyst.

EXAMPLE 6

An oxidic catalyst with the molar ratio Cu:Zn:Al:Mg:Si of 4.3:1.6:1.0:0.2:0.04 and a copper oxide content of 63.9 wt. % was prepared. In a first precipitation step, a mixed metal solution comprising nitrates of copper and zinc, which contained a silica sol, was co-precipitated with a potassium carbonate solution at a pH of 6.4-6.7 and a temperature of 65° C. to form a first precipitate slurry. In a second precipitation step, a mixed metal solution comprising nitrates of aluminium and magnesium was precipitated with a potassium hydroxide solution at a pH of 7.0-7.2 and a temperature of 75° C. to form a second precipitate slurry, and the second precipitate slurry aged at 65° C. for up to 2 hours. The remaining mixing, drying and calcining steps were carried out according to the method of Example 1.

EXAMPLE 7

An oxidic catalyst with the molar ratio Cu:Zn:Al:Mg:Si of 4.3:1.6:1.0:0.2:0.04 and a copper oxide content of 64.2 wt. % was prepared. In a first precipitation step, a mixed metal solution comprising nitrates of copper and zinc was co-precipitated with a potassium carbonate solution at a pH of 6.4-6.7 and a temperature of 65° C. to form a first precipitate slurry. Silica sol was added to the first precipitate slurry. In a second precipitation step, a mixed metal solution comprising nitrates of aluminium and magnesium was precipitated with a potassium hydroxide solution at a pH of 7.0-7.2 and a temperature of 75° C. to form a second precipitate slurry, the second precipitate slurry aged at 65° C. for up to 2 hours. The remaining mixing, drying and calcining steps were carried out according to the method of Example 1.

EXAMPLE 8

An oxidic catalyst with the molar ratio Cu:Zn:Al:Mg:Si of 4.4:1.6:1.0:0.1:0.04 and a copper oxide content of 64.8 wt. % was prepared. In a first precipitation step, a mixed metal solution comprising nitrates of copper, zinc and magnesium was co-precipitated with a potassium carbonate solution containing potassium silicate at a pH of 6.4-6.7 and a temperature of 65° C. to form a first precipitate slurry. In a second precipitation step, a mixed metal solution comprising nitrates of aluminium and zinc was precipitated with a potassium carbonate solution at a pH of 7.0-7.2 and a temperature of 75° C. to form a second precipitate slurry, and the second precipitate slurry aged at 65° C. for up to 2 hours. The remaining mixing, drying and calcining steps were carried out according to the method of Example 1. The first precipitate contained 84 wt % of the total zinc in the calcined catalyst. The second precipitate contained 16 wt % of the total zinc in the calcined catalyst.

EXAMPLE 9

An oxidic catalyst with the molar ratio Cu:Zn:Al:Mg:Si of 4.3:1.6:1.0:0.2:0.04 and a copper oxide content of 63.9 wt. % was prepared. In a first precipitation step, a mixed metal solution comprising nitrates of copper and zinc was co-precipitated with a potassium carbonate solution containing potassium silicate at a pH of 6.4-6.7 and a temperature of 65° C. to form a first precipitate slurry. In a second precipitation step, a mixed metal solution comprising nitrates of aluminium, zinc and magnesium was precipitated with a potassium hydroxide solution at a pH of 7.0-7.2 and a temperature of 75° C. to form a second precipitate slurry, and the second precipitate slurry aged at 65° C. for up to 2 hours. The remaining mixing, drying and calcining steps were carried out according to the method of Example 1. The first precipitate contained 84 wt % of the total zinc in the calcined catalyst. The second precipitate contained 16 wt % of the total zinc in the calcined catalyst.

EXAMPLE 10

An oxidic catalyst with the molar ratio Cu:Zn:Al:Si of 4.6:1.7:1.0:0.03 and a copper oxide content of 65.4 wt. % was prepared. In a first precipitation step, a mixed metal solution comprising nitrates of copper and zinc was co-precipitated with a potassium carbonate solution at a pH of 6.4-6.7 and a temperature of 65° C. to form a first precipitate slurry. In a second precipitation step, a mixed metal solution comprising nitrates of aluminium and copper, which contained a silica sol, was precipitated with a potassium hydroxide solution at a pH of 7.0-7.2 and a temperature of 75° C. to form a second precipitate slurry, and the second precipitate slurry aged at 65° C. for up to 2 hours. The remaining mixing, drying and calcining steps were carried out according to the method of Example 1. The first precipitate contained 94 wt % of the total copper in the calcined catalyst. The second precipitate contained 6 wt % of the total copper in the calcined catalyst.

EXAMPLE 11

An oxidic catalyst with the molar ratio Cu:Zn:Al:Si of 4.6:1.7:1.0:0.03 and a copper oxide content of 65.5 wt. % was prepared. A mixed metal solution comprising nitrates of aluminium and zinc and silica sol was coprecipitated with a potassium hydroxide solution at a pH of 7-7.2 and a temperature of 75° C. to form a precipitate that was aged at 65° C. for 1.3 hours. This precipitate contained 16 wt % of the total zinc oxide content. A mixed metal solution comprising nitrates of copper and zinc, and a potassium carbonate solution, were simultaneously added to the precipitate with stirring, while maintaining a pH of 6.6-6.8 and a temperature of 65-70° C. The final co-precipitated catalyst precursor slurry was aged for 1 hour at 65-70° C., then dewatered, washed with demineralised water, dried and calcined in air at 300° C. for 6 hours.

EXAMPLE 12

An oxidic catalyst with the molar ratio Cu:Zn:Al:Si of 4.5:1.7:1.0:0.03 and a copper oxide content of 65.2 wt. % was prepared. In a first precipitation step, a mixed metal solution comprising nitrates of copper and zinc was co-precipitated with a potassium carbonate solution at a pH of 6.4-6.7 and a temperature of 65° C. to form a first precipitate slurry. In a second precipitation step, a mixed metal solution comprising nitrates of aluminium and zinc, which contained a silica sol, was precipitated with a potassium hydroxide solution at a pH of 4.9-5.1 and a temperature of 70-72° C. to form a second precipitate slurry, and the second precipitate slurry aged at 65° C. for up to 2 hours. The remaining mixing, drying and calcining steps were carried out according to the method of Example 1. The first precipitate contained 84 wt % of the total zinc in the calcined catalyst. The second precipitate contained 16 wt % of the total zinc in the calcined catalyst.

EXAMPLE 13

An oxidic catalyst with the molar ratio Cu:Zn:Al:Mg:Si of 4.3:1.7:1.0:0.1:0.03 and a copper oxide content of 64.0 wt. % was prepared. In a first precipitation step, a mixed metal solution comprising nitrates of copper, zinc and magnesium was co-precipitated with a potassium carbonate solution containing potassium silicate at a pH of 6.4-6.7 and a temperature of 65° C. to form a first precipitate slurry. In a second precipitation step, a mixed metal solution comprising nitrates of aluminium and zinc was precipitated with a potassium hydroxide solution at a pH of 7.0-7.2 and a temperature of 75° C. to form a second precipitate slurry, and the second precipitate slurry aged at 65° C. for up to 1.5 hours. The first precipitate slurry was added to the second precipitate slurry and the remaining ageing, drying and calcining steps were carried out according to the method of Example 1. The first precipitate contained 95 wt % of the total zinc in the calcined catalyst. The second precipitate contained 5 wt % of the total zinc in the calcined catalyst.

EXAMPLE 14

An oxidic catalyst with the molar ratio Cu:Zn:Al:Mg:Si of 4.6:1.8:1.0:0.1:0.04 and a copper oxide content of 64.6 wt. % was prepared. In a first precipitation step, a mixed metal solution comprising nitrates of copper, zinc and magnesium was co-precipitated with a potassium carbonate solution containing potassium silicate at a pH of 6.4-6.7 and a temperature of 65° C. to form a first precipitate slurry. In a second precipitation step, a mixed metal solution comprising nitrates of aluminium and zinc was added to a potassium hydroxide solution to form a second precipitate slurry, and the second precipitate slurry aged at a pH of 6.5-6.8 and temperature of 50° C. for 2.5 hours. The remaining mixing, drying and calcining steps were carried out according to the method of Example 1. The first precipitate contained 84 wt % of the total zinc in the calcined catalyst. The second precipitate contained 16 wt % of the total zinc in the calcined catalyst.

COMPARATIVE EXAMPLE 1

An oxidic catalyst with the molar ratio Cu:Zn:Al:Si of 3.3:1.5:1.0:0.01 and a copper oxide content of 60.1 wt. % was prepared following the procedure outlined in CN101306369 Example 5 by co-precipitating an aluminium nitrate solution with a solution of sodium carbonate and sodium silicate at a pH of 7-7.2 and a temperature of 80° C., and ageing this precipitate at 65° C. for 40 minutes to form an alumina-silica slurry. Separately, a mixed metal solution comprising nitrates of copper and zinc was co-precipitated with a sodium carbonate solution at a pH of 7.0-7.2 and a temperature between 65-70° C. to form a Cu—Zn hydroxycarbonate slurry. The alumina-silica slurry was added to the Cu—Zn hydroxycarbonate slurry in a 1:7 ratio by volume, and the mixture was aged at 70° C. with stirring for 2 hours. The slurry was dewatered, washed with demineralised water, then dried and calcined in air at 340° C. for 4 hours.

COMPARATIVE EXAMPLE 2

An oxidic catalyst with the molar ratio Cu:Zn:Al:Si of 5.8:2.0:1.0:0.03 and a copper oxide content of 68.1 wt. % was prepared. In a first precipitation step, a mixed metal solution comprising nitrates of copper and zinc was co-precipitated with a sodium carbonate solution at a pH of 6.4-6.7 and a temperature of 65° C. to form a first precipitate slurry. In a second precipitation step, a solution of aluminium nitrate was precipitated with a sodium hydroxide solution, which contained sodium silicate, at a pH of 7.0-7.2 and a temperature of 75° C. to form a second precipitate slurry, and the second precipitate slurry aged at 65° C. for up to 2 hours. The second precipitate slurry was added to the first precipitate slurry, and the mixture was aged at 70° C. with stirring for up to 2 hours. The slurry was dewatered, washed with demineralised water, then dried and calcined in air at 300° C. for 6 hours.

COMPARATIVE EXAMPLE 3

An oxidic catalyst with the molar ratio Cu:Zn:Al:Si of 3.8:2.2:1.0:0.04 and a copper oxide content of 56.6 wt. % was prepared following the procedure outlined in U.S. Pat. No. 6,048,820 Example 2. A mixed metal nitrate solution containing nitrates of copper, zinc and aluminium and a silica sol, and a solution of sodium carbonate were added simultaneously to demineralised water in a stirred vessel at room temperature. The resulting precipitate was aged at room temperature for 24 hours, dewatered, washed with demineralised water, dried and calcined in air at 600° C. for 2 hours.

COMPARATIVE EXAMPLE 4

An oxidic catalyst with the molar ratio Cu:Zn:Al of 4.3:1.6:1.0 and a copper oxide content of 65.2 wt. % was prepared. In a first precipitation step, a mixed metal solution comprising nitrates of copper and zinc was co-precipitated with a potassium carbonate solution at a pH of 6.4-6.7 and a temperature of 65° C. to form a first precipitate slurry. In a second precipitation step, a mixed metal solution comprising nitrates of aluminium and zinc was precipitated with a potassium hydroxide solution at a pH of 7.0-7.2 and a temperature of 75° C. to form a second precipitate slurry, and the second precipitate slurry aged at 65° C. for 1.5 hours. The remaining mixing, drying and calcining steps were carried out according to the method of Example 1. The first precipitate contained 84 wt % of the total zinc in the calcined catalyst. The second precipitate contained 16 wt % of the total zinc in the calcined catalyst.

COMPARATIVE EXAMPLE 5

An oxidic catalyst with the molar ratio Cu:Zn:Al:Si of 4.4:1.6:1.0:0.18 and a copper oxide content of 64.1 wt. % was prepared. In a first precipitation step, a mixed metal solution comprising nitrates of copper and zinc was co-precipitated with a potassium carbonate solution at a pH of 6.4-6.7 and a temperature of 65° C. to form a first precipitate slurry. In a second precipitation step, a mixed metal solution comprising nitrates of aluminium and zinc, which contained a silica sol, was precipitated with a potassium hydroxide solution at a pH of 7.0-7.2 and a temperature of 7500 to form a second precipitate slurry, and the second precipitate slurry aged at 65° C. for 2 hours. The second precipitate slurry was added to the first precipitate slurry, and the mixture was aged at 70° C. with stirring for up to 45 minutes. The slurry was dewatered, washed with demineralised water, then dried and calcined in air at 300° C. for 6 hours. The first precipitate contained 84 wt % of the total zinc in the calcined catalyst. The second precipitate contained 16 wt % of the total zinc in the calcined catalyst.

The catalyst properties were as follows:

| Example | Malachite crystallite size (nm) | Copper surface area ($m^2$/g catalyst) | BET surface area ($m^2$/g, compacted) | $SiO_2$ (wt %) |
|---|---|---|---|---|
| Example 1 | 7.4 | 51 | 115 | 0.38 |
| Example 2 | 7.2 | 53 | 121 | 0.36 |
| Example 3 | 9.4 | 43 | 130 | 0.80 |
| Example 4 | 7.0 | 53 | 106 | 0.31 |
| Example 5 | 6.2 | 62 | 112 | 0.32 |
| Example 6 | 6.7 | 61 | 105 | 0.44 |
| Example 7 | 6.1 | 61 | 100 | 0.42 |
| Example 8 | 4.0 | 45 | 77 | 0.40 |
| Example 9 | 7.2 | 54 | 107 | 0.45 |
| Example 10 | 7.0 | 43 | 115 | 0.36 |
| Example 11 | 9.1 | 45 | 104 | 0.34 |
| Example 12 | 7.2 | 55 | 113 | 0.34 |
| Example 13 | 5.0 | 63 | 132 | 0.36 |
| Example 14 | 6.2 | 65 | 106 | 0.38 |
| Comparative Example 1 | n/a | 40 | 104 | 0.20 |
| Comparative Example 2 | 24.0 | 39 | 66 | 0.28 |
| Comparative Example 3 | n/a | 35 | 99 | 0.48 |
| Comparative Example 4 | 7.4 | 51 | 119 | 0.00 |
| Comparative Example 5 | 7.3 | 52 | 114 | 2.00 |

Microreactor Testing

Each of the catalyst samples were crushed and sieved to a particle size fraction of 0.6-1.0 mm. The experiments used a conventional micro-reactor. The crushed catalyst samples were fully reduced with a gas mixture of 2% v/v hydrogen in nitrogen at 225° C. A process gas mixture with a gas composition of 6% v/v CO, 6% v/v $CO_2$, 9% v/v $N_2$ and 79% v/v $H_2$ was then introduced over the catalyst samples. This process gas mixture is representative of a synthesis gas produced by reforming of natural gas. The reduced catalyst samples were exposed to the process gas mixture at 225° C., 40,000 L/hr/kg, 50 barg at the start of life. After a period, catalyst samples were exposed to deactivating conditions over 300° C. to simulate harsh operating conditions and accelerate the deactivation effects. Analysis flow scans of product gases were performed at the start of life and after the catalyst had been held at deactivation conditions. Analysis flow scans were performed by varying the mass velocity at 225° C., 50 barg. An infra-red analyser was used to determine the % v/v concentration of the exit gas streams from the reactors. The analysis flow scan data was used to calculate the relative activity of the test material against a reference catalyst, selected in these experiments to be Comparative Example 1. The relative activities are calculated from the ratio of the flow rates through each catalyst at constant conversion relative to the flow rate through the standard catalyst. The results are set out in the following table:

| Example | Activity at 16 hours on-line relative to comparative example 1 | Activity at 210 hours on-line relative to comparative example 1 |
|---|---|---|
| Example 1 | 1.32 | 1.51 |
| Example 2 | 1.52 | 1.55 |
| Example 3 | 1.29 | 1.39 |
| Example 4 | 1.33 | 1.44 |
| Example 5 | 1.48 | 1.64 |
| Example 6 | 1.28 | 1.37 |
| Example 7 | 1.26 | 1.38 |
| Example 8 | 0.87 | 1.40 |
| Example 9 | 1.25 | 1.51 |
| Example 10 | 1.21 | 1.51 |
| Example 11 | 1.20 | 1.39 |
| Example 12 | 1.37 | 1.49 |
| Example 13 | 1.48 | 1.56 |
| Example 14 | 1.44 | 1.50 |
| Comparative Example 1 | 1.00 | 1.00 |
| Comparative Example 2 | 0.79 | 0.96 |
| Comparative Example 3 | 0.90 | 1.11 |
| Comparative Example 4 | 1.29 | 1.15 |
| Comparative Example 5 | 1.28 | 0.86 |

The testing results show that catalysts made via methods of the invention possess both higher initial activity and higher retained activity, following a period of high temperature deactivation under methanol synthesis conditions than catalyst made via prior methods (comparative examples 1 and 3). This is a result of the small malachite crystallite size, the optimised support phase and the stabilising effect of silica.

Comparative example 2 exemplifies the requirement for a second metal to be included in the second precipitation with aluminium. Comparative example 4 exemplifies that the silica-free formulation has inferior long-term activity compared to Si-containing formulations. Comparative example 5 shows that higher silica loadings can be detrimental to long-term catalyst performance.

In addition to the above tests carried out with a conventional synthesis gas, further microreactor tests were also carried out on the catalyst of Example 5 to evaluate performance under conditions appropriate for $CO_2$ hydrogenation. In this case, following reduction as above, the samples were exposed to a process gas mixture with a composition of 16% v/v $CO_2$, 2% v/v CO, 10% v/v $N_2$ and 72% v/v $H_2$, initially at 225° C., 70,000 L/hr/kg and 50 barg. After a period, the samples were exposed to deactivation conditions above 265° C. to simulate harsh operation and accelerate deactivation. As in the previous testing, flow scans were periodically carried out throughout the run at the milder conditions in order to monitor the remnant activity of the samples. The results obtained are shown in the following table, again with the Comparative example 1 as the reference catalyst:

| Example | Activity at 164 hours on-line relative to comparative example 1 | Activity at 400 hours on-line relative to comparative example 1 |
|---|---|---|
| Example 5 | 1.23 | 1.37 |
| Comparative Example 1 | 1.00 | 1.00 |

These testing results again show that catalysts made via methods of the invention possess both higher initial activity and higher retained activity, following a period of high temperature deactivation under $CO_2$ hydrogenation to methanol conditions, than catalyst made via prior methods.

The invention claimed is:

1. A method for preparing a copper-containing catalyst comprising the steps of: (a) combining an acidic copper-containing solution with a first basic precipitant solution in a first precipitation step to form a first precipitate, (b) combining an acidic aluminium-containing solution, further comprising one or more metal compounds selected from copper compounds, zinc compounds and promoter compounds, with a second basic precipitant solution in a second precipitation step to form a second precipitate, (c) contacting the first and second precipitates together in a further mixing step to form a catalyst precursor, and (d) washing, drying and calcining the catalyst precursor to form the copper-containing catalyst, wherein a silica precursor is included in the first precipitation step, the second precipitation step or the precipitate mixing step, to provide a catalyst with a silica content, expressed as $SiO_2$, in the range of 0.1 to 5.0 wt %.

2. The method according to claim 1, wherein the first precipitation step is performed by combining an aqueous acidic copper-containing solution containing copper and zinc compounds with an aqueous alkali metal carbonate solution in a first precipitation vessel.

3. The method according to claim 2, wherein the copper and zinc compounds are nitrates and the alkali metal carbonate comprises sodium carbonate or potassium carbonate.

4. The method according to claim 1, wherein copper compounds are included in both the first precipitation step and the second precipitation step and the amount of copper in the second precipitation step is in a range of 0.5 to 20 wt % of the total copper added.

5. The method according to claim 1, wherein zinc compounds are included in both the first precipitation step and the second precipitation step and the amount of zinc in the second precipitation step in in a range of 0.5 to 50 wt % of the total zinc added.

6. The method according to claim 1, wherein one or more promoter compounds selected from compounds of Mg, Co, Mn, V, Ti, Zr or rare earths, are included in the acidic copper-containing solution in the first precipitation step and/or the acidic aluminium-containing solution in the second precipitation step.

7. The method according to claim 1, wherein the first precipitation step is performed at a temperature in a range of 40 to 80° C., and a pH range of 6-8.

8. The method according to claim 1, wherein the second precipitation step is performed by combining an aqueous solution containing aluminium nitrate and one or more metal nitrates selected from copper nitrate, zinc nitrate and promoter metal nitrate with an aqueous alkali metal hydroxide solution.

9. The method according to claim 1, wherein the second precipitation step is performed at a temperature in a range of 10 to 80° C., and at a pH in the range of 5-9.

10. The method according to claim 1, wherein the second precipitate formed in step (b) and/or the combined precipitates in step (c) are aged at a temperature in a range of 10 to 80° C.

11. The method according to claim 1, wherein step (a) is performed before or after step (b), or step (a) and step (b) are performed simultaneously.

12. The method according to claim 1, wherein neither of the precipitates from steps (a) and (b) are separated and washed prior to the combining step (c).

13. The method according to claim 1, wherein in step (c) slurries of the first and second precipitates are combined in a mixing vessel.

14. The method according to claim 1, wherein step (c) is performed at the same time as step (a) or step (b).

15. The method according to claim 1, wherein the catalyst has a silica content, expressed as $SiO_2$, in a range of 0.1 to 3.0 wt %.

16. The method according to claim 1, wherein the silica precursor is a colloidal silica or silica sol, a water-soluble silicon compound, an alkali metal silicate, or an organosilicate.

17. The method according to claim 1, wherein an acidic silica sol is included in the acidic copper-containing solution in the first precipitation step, the acidic aluminium-containing solution in the second precipitation step, the first precipitate, the second precipitate or a mixture of the first and second precipitates in the precipitate mixing step.

18. The method according to claim 1, wherein an alkali metal silicate or a basic silica sol is included in the first basic precipitant solution in the first precipitation step, the second basic precipitant solution in the second precipitation step, the first precipitate, the second precipitate or to a mixture of the first and second precipitates in the precipitate mixing step.

19. The method according to claim 1 wherein the drying is performed at a temperature in he a range of 90-150° C.

20. The method according to claim 1 wherein the calcination is performed at a temperature in a range of 250° C. to 500° C.

21. The method according to claim 1 wherein the dried or calcined catalyst precursor is shaped by pelleting.

22. The method according to claim 1, wherein one or more zinc compounds are included in the first precipitation step and the second precipitation step, and the weight ratio of Cu:Zn (expressed as CuO:ZnO) in the copper-containing catalyst is in a range of 2:1 to 3.5:1 for methanol synthesis catalysts, and in a range of 1.4:1 to 2.0:1 for water-gas shift catalysts.

23. The method according to claim 1, wherein the copper-containing catalyst comprises 30-70% by weight of copper, expressed as CuO, 15 to 50% by weight of Zn, expressed as ZnO, 5 to 40% by weight alumina, expressed as $Al_2O_3$, 0 to 5% by weight magnesia, expressed as MgO, and 0.1 to 2.0% by weight Si, expressed as $SiO_2$.

24. The method according to claim 1, wherein the copper-containing catalyst comprises 50 to 68% by weight of copper, expressed as CuO, 20 to 35% by weight of Zn, expressed as ZnO, 6 to 20% by weight alumina, expressed as $Al_2O_3$, 0 to 5% by weight magnesia, expressed as MgO, and 0.20 to 1.0% by weight Si, expressed as $SiO_2$.

25. A catalyst obtainable by the method of claim 1.

26. A process comprising contacting a methanol synthesis feedstock a methanol reforming feedstock, or a water-gas shift feedstock with the catalyst of claim 25.

27. The method according to claim 1, wherein the catalyst has a silica content, expressed as $SiO_2$, in a range of 0.1 to 2.0 wt %.

28. The method according to claim 1, wherein the catalyst has a silica content, expressed as $SiO_2$, in a range of 0.2 to 1.0 wt %.

* * * * *